United States Patent [19]

Batchelor et al.

[11] 4,095,473
[45] Jun. 20, 1978

[54] PYCNOMETER

[75] Inventors: Robert L. Batchelor, Orange; Thomas J. Lynch, Houston, both of Tex.

[73] Assignee: Gulf Oil Corporation, Pittsburgh, Pa.

[21] Appl. No.: 797,648

[22] Filed: May 16, 1977

[51] Int. Cl.² .............................................. G01N 9/02
[52] U.S. Cl. ........................................ 73/433; 526/59
[58] Field of Search ............................ 73/433, 32 R; 260/33.6 PQ; 526/59

[56] References Cited

U.S. PATENT DOCUMENTS

| 2,978,441 | 4/1961 | Sherk | 526/59 |
| 3,492,283 | 1/1970 | Miller | 526/59 |
| 3,595,840 | 7/1971 | Moberly | 526/59 |

Primary Examiner—Richard C. Queisser
Assistant Examiner—Stephen A. Kreitman
Attorney, Agent, or Firm—Richard L. Kelly

[57] ABSTRACT

The invention is directed to a pycnometer designed to measure the density of particulate porous polymer samples, particularly polymer samples having hydrocarbons and/or air absorbed in the pores thereof. The apparatus includes a sample cell of fixed volume fitted with a sample container of fixed weight, a gas reservoir of fixed volume, a valved line providing gas communication between the sample cell and the gas reservoir, a linear variable differential transducer to measure the weight of the polymer sample in the sample cell, a variable capacitance quartz crystal for measuring gas pressure in the gas reservoir, and a computer which calculates the density of the sample from the sample weight, and the volume of the sample determined by measurement of a super-atmospheric gas pressure in the gas reservoir when isolated from the sample cell and the equalized pressure established when the gas reservoir is placed in open communication with the sample cell. An output signal from the computer indicative of the sample's density can be fed to a light-emitting diode or a printer, or to a process control computer to make any required adjustments in a polymerization reactor to produce polymer within a preselected range of polymer density.

10 Claims, 4 Drawing Figures

PYCNOMETER

BACKGROUND OF THE INVENTION

In the manufacture of high density olefin polymers such as linear ethylene polymers, it is desirable to manufacture such polymers in a range of densities. The density of such polymers can be controlled by copolymerizing varying quantities of a higher monoolefin such as butene or hexene with the ethylene. The density of such copolymers is inversely proportional to the quantity of the higher monoolefin comonomer copolymerized with the ethylene.

It would be desirable to monitor such copolymerization processes by periodically measuring the density of the copolymer being produced and making any indicated changes in the rate of comonomer fed to the reactor to produce copolymer within a preselected range of density. Several problems are encountered, however, which preclude the measurement of copolymer density as a tool to control the density of the copolymer being produced. The first problem is that such polymers as recovered are porous and have a very low bulk density. The samples also have hydrocarbons absorbed in their pores which interferes with accurate determination of density. It has been found that to obtain density values which correlate with polymer properties, it is necessary to extrude the recovered polymer, prepare samples for density determinations, and anneal such samples so that the polymer will crystallize to obtain its maximum density. The preparation of such samples is so time consuming as to render this method inappropriate for use as an online process control parameter. The second problem in using density measurements as a process control parameter is that the presently preferred method for measuring such polymer densities (a density-gradient technique as set forth in ASTM Method D1505-63T) is laborious and time consuming.

For the reasons discussed above, there is a need in the art for apparatus and methods for rapidly determining the density of olefin polymers, particularly porous olefin polymers having hydrocarbons and/or air absorbed in the pores thereof.

BRIEF DESCRIPTIONS OF DRAWINGS

SUMMARY OF THE INVENTION

By the present invention, the applicants have provided apparatus which is capable of providing highly accurate determination of densities of porous olefin polymers in a relatively short period of time. The apparatus includes a sample cell of fixed volume having lines for admitting and discharging gas therefrom. The sample cell includes a sample container of fixed weight. The sample cell also includes instrument means which measures the weight of the sample container and generates a signal indicative thereof; the presently preferred embodiment of such instrument means being a linear variable differential transducer. The apparatus includes a gas reservoir of fixed volume having lines to admit and discharge gas therefrom. A valved line provides gas communication between the sample cell and the gas reservoir. Second instrument means are associated with the gas reservoir which measure the gas pressure therein and generate a signal indicative thereof; a presently-preferred embodiment of such instrument means being a variable capacitance quartz crystal. The signals from the two instrument means are fed to a computer. The computer has the capability of determining the sample's weight from the signal received from the first instrument means and information respecting the weight of the sample cell stored in the computer. From information contained in its memory respecting the volume of the gas reservoir and the empty sample cell and the signals received from the second instrument means, the computer can calculate the true volume of the sample. From these determinations, the computer calculates the true density of the sample and generates a signal indicative thereof. The output signal from the computer can be fed to either a light-emitting diode, or a printer to indicate the density of the sample. If desired, the output signal of the computer can be fed to a process control computer for controlling the feed of the comonomer to a polymerization reactor producing the olefin copolymers whose densities are being determined.

DETAILED DESCRIPTION OF THE INVENTION

Figure 1:
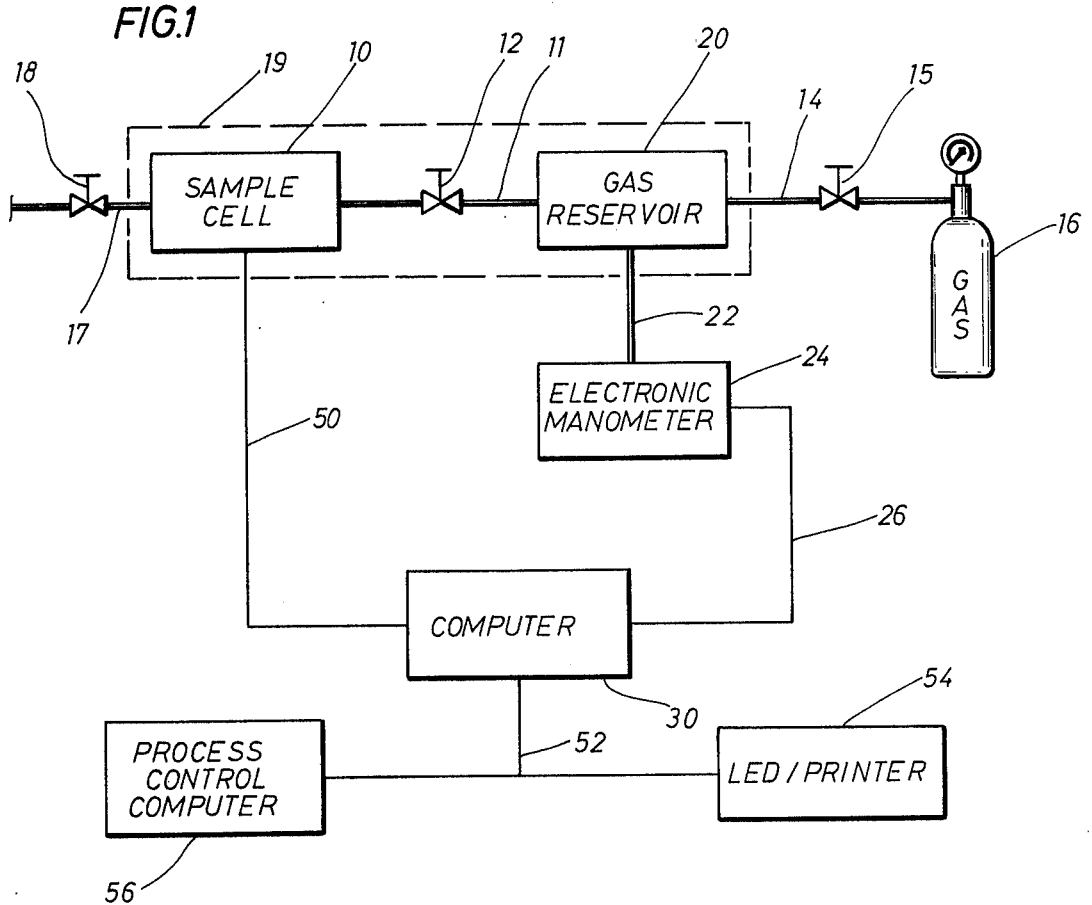
FIG. 1 is a schematic block diagram of a pycnometer constructed in accordance with the invention.

FIG. 1 is a schematic diagram of a pycnometer made in accordance with the present invention. The apparatus includes a sample cell 10 of known volume and a gas reservoir 20 of known volume. Sample cell 10 and gas reservoir 20 are joined by line 11 including valve 12 therein. A line 14, including valve 15, connects gas reservoir 20 to a gas cylinder 16. A line 17, including valve 18, is provided for discharging gas from sample cell 10. The sample cell 10 and the gas reservoir 20 are sealed in a chamber 19 maintained at a constant and uniform temperature. A line 22 connects gas reservoir 20 to an electronic monometer 24 which measures the pressure within gas reservoir 20. Electronic monometers having a capability of reading pressure with an accuracy of ±0.0005 psi can be purchased from commercial sources such as Setra Systems, Inc., of Natick, Mass. The electronic monometer 24 generates a signal indicative of the gas pressure which is fed by a cable 26 to a computer 30. A cable 50 is provided and contains a plurality of lines which feeds electrical signals between the instrument means in the sample cell and the computer 30. Additional lines (not shown) from the computer 30 carry signals as required to open and close valves 12, 15, and 18. Thermocouples (not shown) are provided in the sample cell 10 and the gas reservoir 20 and feed signals to the computer 30 to indicate the prevailing gas temperature. A cable 52 is provided and carries a number of electrical lines to display sample weights and/or densities in a display device 54, such as a light-emitting diode or a printer. Cable 52 also may carry lines which feed output signals to a process control computer 56.

Figure 2:
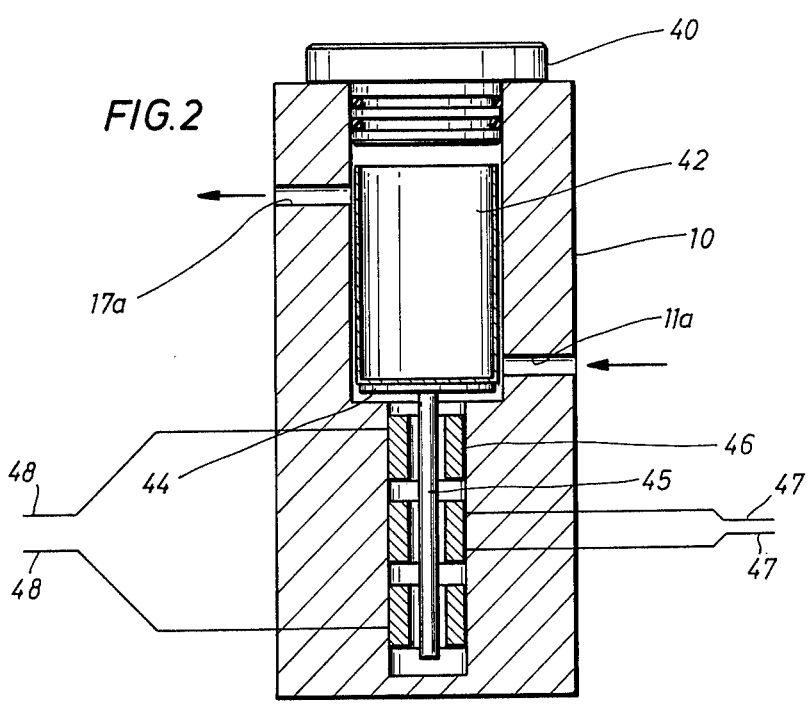
FIG. 2 is a sectional view of one embodiment of a sample cell and sample container that can be employed in the apparatus of FIG. 1.

FIG. 2 sets forth the structure of a sample cell suitable for use in the apparatus of FIG. 1. The sample cell 10 is cylindrical in shape and includes tapped ports 11a and 17a which connect to, respectively, lines 11 and 17.

A threaded cap 40 is provided so that a cylindrical sample container 42 can be placed in and removed from the sample cell. The sample container 42 rests upon pan 44 of a linear variable differential transducer (LVDT). The linear variable differential transducer is of a conventional null point design. The pan 44 is mounted on a magnetized core rod 45 which is maintained in a fixed position by varying the strength of the magnetic field in which it is placed. The strength of the magnetic field is controlled by varying the current which energizes electromagnets 46. The electrical circuits which control the strength of the magnetic field are not shown in detail, but they include lines 47 which carry a current to the primary coil of a transformer which adjusts the strength of the magnetic field as required to maintain magnetized core rod 45 in its fixed position. The input voltage of lines 47 varies with the weight in the sample cell 42. Lines 48 are the output lines of a secondary coil of the transformer. The output voltage of lines 48 varies with the input voltage of lines 47 and thus also is a function of the weight of the sample cell 42.

After the sample is placed in sample cell 40 of the apparatus of FIG. 1, the computer 30 is engaged and a series of sequential operations is carried out automatically. Valve 18 is closed and valves 12 and 15 are opened to pressurize the sample cell with helium. Typically the helium pressure will be set at about 30 psig. Valve 12 then is closed and valve 18 is opened to vent the sample cell to atmospheric pressure. When the sample cell is pressurized with helium, the helium, by reason of its small molecular size, enters into the pores of the sample and displaces the hydrocarbon and/or air previously absorbed in the pores of the sample. The displacement of the hydrocarbon and/or air from the sample changes the sample weight and the output signal generated by the LVTD indicates the sample weight to the computer 30. The pressurizing and venting of the sample cell with helium is repeated until the sample reaches a constant weight. Typically this operation is repeated until three consecutive weighings agree to within a preselected tolerance of about ±0.001 gram. At this point, the computer stores the measured weight in its memory.

After the sample has reached constant weight, valves 12 and 18 are closed and valve 15 is opened to pressurize gas reservoir 20 to a pressure of the order of about 30 psig. At this point, valve 15 is closed and a signal from electronic monometer 24 indicative of the gas pressure is fed by cable 26 to the computer 30. This pressure reading is placed in the computer's memory. The gas temperature, indicated by lines from a thermal couple also carried in cable 26, also is stored in the computer's memory. Valve 12 then is opened and an equalized pressure is generated in the gas reservoir 20 and the sample cell 10. A second signal from the electronic monometer 24 is fed to computer 30. The gas pressure indicated by this second signal is placed in the computer's memory, together with the gas temperature which is measured as previously described.

The volumes of the gas reservoir 20 and the empty sample cell 10 are known from prior calibrations and are stored in the computer's memory. From the known volume of the gas reservoir, the two pressures read the electronic monometer 24 and the known relationship between pressure and volume at a fixed temperature (the perfect gas law), the computer calculates the combined volume of the filled sample cell and the gas reservoir. The computer makes any required temperature correction from the two temperature readings placed in the memory.* This volume then is subtracted from the known volume of the empty sample cell and the gas reservoir. This calculated difference in volume is the volume of the porous sample after all of the hydrocarbon and/or air contained in its pores has been displaced with helium. From the weight of the sample previously measured by the LVTD and the determined volume of the sample, the computer calculates the polymer's density.

* The calculated sample volume is essentially independent of the initial pressure in the sample cell, which is atmospheric pressure. For maximum accuracy, atmospheric pressure can be measured by monometer 24 and a signal fed to the computer 30 which makes a minor adjustment for small variations in atmospheric pressure.

To insure maximum accuracy, the calculated density is stored in the computer's memory and all operations are repeated to obtain one or more additional measurements of the sample's density. When a preselected number of measurements within a predetermined range of precision are obtained, the computer generates an output signal indicative of the sample's density, such signal being an average reading of all of or selected individual determinations. The output signal is fed by cable 52 to a suitable display instrument 54 which can be, inter alia, a light-emitting diode or a printer. Where desired, the output signal can be fed by cable 52 to a process control computer for controlling the polymerization which is manufacturing the porous polymer samples whose densities are being determined by the apparatus of FIG. 1.

Figure 3:
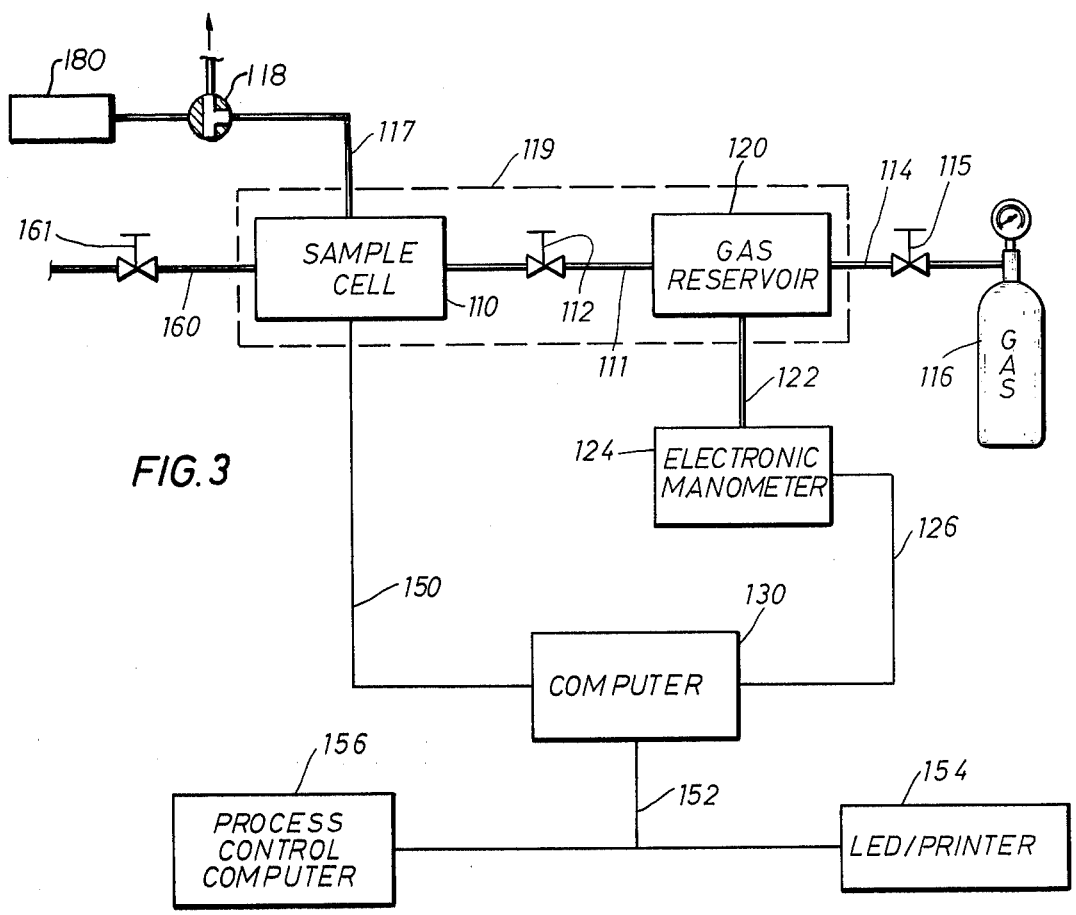
FIG. 3 is a schematic block diagram of a pycnometer which includes elements to feed porous polymer samples directly from a polymerization reactor to the sample cell.
Figure 4:
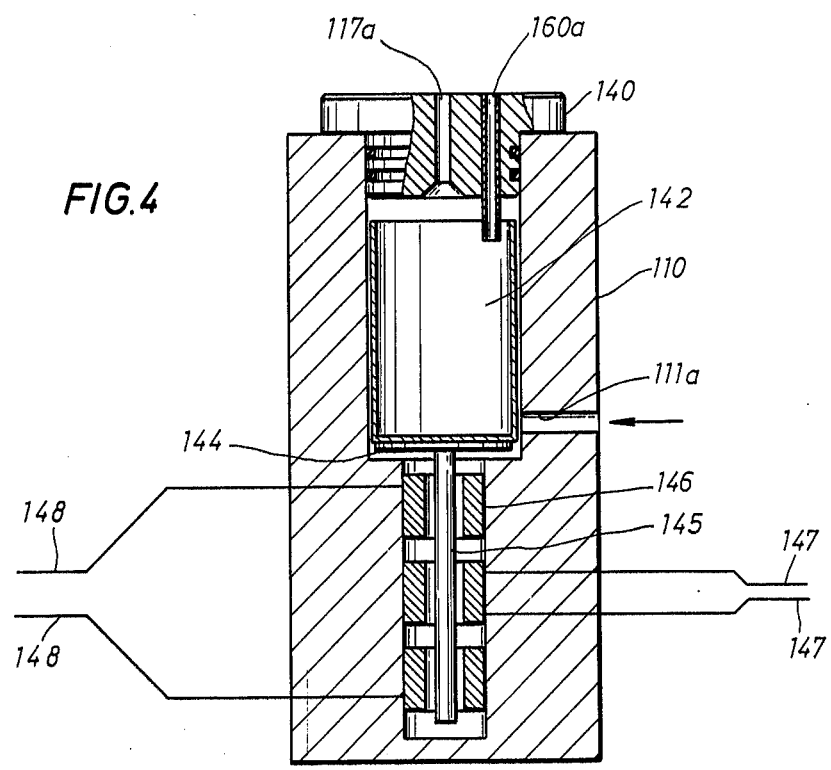
FIG. 4 is a sectional view of one embodiment of a sample cell and sample container that can be employed in the apparatus of FIG. 3.

FIGS. 3 and 4 illustrate a modification of the apparatus illustrated in FIGS. 1 and 2. Specifically, the construction of the sample cell illustrated in FIG. 4 is modified to transfer polymer samples into and out of the sample container without removing the sample container from the sample cell. This embodiment is designed for use to continuously monitor the density of ethylene copolymers from a continuous polymerization reactor and to employ the density data so obtained to control the feed of comonomer to such ethylene copolymerization.

In FIGS. 3 and 4, the parts and elements that correspond to like parts and elements of FIGS. 1 and 2 bear numbers 100 units greater than the corresponding parts and elements of FIG. 1. Thus, in FIG. 3 the gas reservoir bears number 120, the electronic monometer bears number 124, the sample cell bears the number 110, and so forth. In addition to common components and elements, the apparatus of FIGS. 3 and 4 also includes a line 160, having a valve 161 therein, which feeds into tapped line 160a which is located in cap 140 and which terminates within the sample container 142. Line 117 connects to tapped port 117a which also is located in cap 140.

In the operation of the apparatus illustrated in FIGS. 3 and 4, a slurry of an ethylene copolymer in a low boiling hydrocarbon, such as isobutane, is pneumatically fed from a reactor not shown through line 160 so as to substantially fill the sample container 142. Valve 161 then is closed. Valve 118 is opened to atmospheric pressure so that the low boiling hydrocarbon introduced into the sample container 142 is vented. It is not necessary to vent all of the hydrocarbon at this time, as any residual hydrocarbon in the sample cell will be displaced in the subsequent operations which determine the sample's density. Valve 118 then is closed and the density of the sample is determined by the series of sequential operations previously described and which are carried out automatically by the computer 130. In this embodiment of the invention, the output signal from computer 130 indicative of the polymer's density is fed through cable 152 to the process control computer 156, which makes any indicated adjustment in the feed of comonomer being employed to prepare the ethylene polymer copolymer whose density was determined. The signal indicative of the density of the sample also will be fed to the light-emitting diode, or printer 154.

After the density of a sample has been determined, valves 112 and 161 are closed. Three way valve 118 then is opened to vacuum source 180 which withdraws the porous polymer sample from the sample cell through line 117. The computer 130 receives output signals from the LVDT which are indicative of the weight of sample container 142. The signals are compared with the known weight of sample cell 152 which is stored in the computer's memory. When the sample cell 142 reaches its normal tare weight, all of the polymer sample has been evacuated from the sample container. The computer then sends a signal which changes the setting of valve 118 so that line 117 is opened to atmospheric pressure. The apparatus now is in a condition to determine the density of the next sample to be fed to the apparatus.

In the drawings and the above descriptions, it has been stated that the various operations are directed and controlled by a computer. It is generally understood that a computer is programmable and its mode of operation can be varied after it is constructed. Devices which can be constructed with a fixed program including memory elements, but which are not subsequently programmable once assembled, frequently are referred to in the art as microprocessors. Microprocessors can be substituted for computers in the apparatus of the invention where the apparatus is to be designed to carry out only preselected operations.

It also will be recognized that various equivalent elements can be substituted for the elements specifically illustrated and described. In the two embodiments of a sample cell illustrated in FIGS. 2 and 4, the sample container rests upon the pan of the LVDT. It is equally feasible to construct the sample cell with the opening located at the bottom of the sample cell, with the LVDT being positioned at the top of the sample cell and being provided with a hook. In this modification, a suitable handle will be mounted on the sample container which will then be placed on the hook of the magnetized core of the LVDT. It also is recognized that other sensitive weighing mechanisms can be substituted for the LVDT, including instruments which utilize a null magnetic coil plus a variable capacitor system to generate a signal that can be equated to the weight of the sample container. For general reference to sophisticated instrument systems which can be employed in the apparatus of the invention to measure weight and pressure, see the text *Fundamentals of Temperature, Pressure, and Flow Measurements* by Robert P. Benedict, Copyright 1969 by John Wiley & Sons, Inc., Library of Congress Catalog Card No. 68-9244 SBN 471 06560 X. To enhance the accuracy of the apparatus, the volumes of the gas reservoir and the sample cell should be approximately the same to maximize the differentials in pressure used to calculate the sample volume.

While it is apparent that the apparatus of the invention can be employed to determine the density of a wide variety of particulate solids, through a combination of fortuitous circumstances, the apparatus finds particular utility in determining the density of porous olefin polymers, particularly polymer samples having hydrocarbons absorbed in the pores of the polymer. Olefin polymers of this type are produced when such olefin polymers are prepared by a so-called particle form process as described in coapplicant Lynch's pending U.S. patent application Ser. No. 722,197, filed Sept. 10, 1976, and assigned to the assignee of the present application.

As noted earlier in this application, certain performance characteristics of olefin copolymers are influenced by the density of the olefin copolymers. Since the density of the copolymers is influenced by the method by which the density is determined (by reason of the fact that olefin polymers can assume various crystalline structures depending upon the rate at which the olefin copolymer is cooled), all density specifications for such copolymers are based upon so-called annealed density values as conventionally measured by ASTM Method D 1505-63-T. It is reported in the literature that annealed olefin polymers are present in the so-called folded chain form.

A number of literature sources have suggested that olefin polymers produced by polymerization in the presence of Ziegler-type catalysts, or chromia on silica catalysts, are produced in an extended chain crystal form. Three such references are B. Wunderlich, ADV. Polymer Sci., 5, 602–606 (1968) T. Davidson, Polymer Letters, 8, 885, (1970); and H. Chanzy, et al., Polymer, 8, 567 (1976). It is known that olefin polymers in the extended chain crystal form have a lower density than the same polymers present in their folded chain form. Accordingly, based upon the information contained in the literature, it would not have been expected that direct measurement of density of olefin copolymers as produced in a particle form polymerization would give density values which would be directly correlatable with annealed density values which the art employs as a performance specification for olefin copolymers. Surprisingly, however, the applicants' work has clearly indicated that the values obtained with their apparatus and by their methods do give density values directly correlatable with densities obtained by ASTM Method D 1505-63T.

To obtain accurate density values on olefin polymers which correlate well with annealed density values determined by ASTM Method D 1505-63T, it is believed important to employ helium as the gas to alternatively pressurize and depressurize the porous olefin polymer samples. Helium has a uniquely small molecular size and can enter into the pores of the polymer sample so as to displace hydrocarbons and possibly air which may be absorbed in the polymer sample. It is necessary to displace such materials from the pores of the sample to obtain accurate and reproducible density determinations.

The following examples are set forth to illustrate the principle and practice of the invention to those skilled in the art. Except where otherwise noted, where parts and percentages are mentioned they are parts and percentages by weight.

EXAMPLE I

Apparatus conforming to that illustrated in FIGS. 1 and 2 was constructed except that the computer and the LTVD of the sample cell were not placed in operation. The sample cell had a volume of 135 ml and the gas reservoir had a volume of 70 ml. The electronic monometer employed was built by Setra Systems and utilized a fused quartz variable capacitance sensor capable of reproducible readings of ±0.0005 psig.

Two technicians unfamiliar with the apparatus and method were instructed in its operation and directed to determine the density on thirteen samples of ethylene-hexene-1 copolymers prepared in a pilot plant particle form loop reactor. The experimental results are set forth in Table I.

Table I

| Sample | Sample Wt, g | $P_1$, mmHg[1] | $P_2$, mmHg[2] | Temp° C | Pressure Ratio[3] | STD DEV[4] | Density g/cc | Percent Error[5] |
|---|---|---|---|---|---|---|---|---|
| | | | | | Observed Precision of Inexperienced Operators | | | |
| 1 | 48.61276 | 49.25 | 32.59 | 23.8 | 1.511998 | | | |
| | | 49.68 | 32.88 | 23.9 | 1.510949 | | | |
| | | 49.12 | 32.51 | 24.0 | 1.510919 | | | |
| | | 40.42 | 32.69 | 24.1 | 1.511777 | | | |
| | | 49.64 | 32.84 | 24.0 | 1.511571 | | | |
| | | | | | Avc 1.5114428 | ±0.0004883 | .9536 ±0.0003 | 0.0323 |
| 2 | 52.33768 | 49.67 | 33.32 | 24.1 | 1.400696 | | | |
| | | 49.90 | 33.47 | 24.2 | 1.490887 | | | |
| | | 49.78 | 33.39 | 24.3 | 1.490865 | | | |
| | | 49.83 | 33.42 | 24.3 | 1.491023 | | | |
| | | 49.75 | 33.36 | 24.4 | 1.491306 | | | |
| | | | | | Avc 1.400955 | ±0.0002278 | .9536 ±0.0001 | 0.0152 |
| 3 | 57.73925 | 49.35 | 33.78 | 24.6 | 1.460923 | | | |
| | | 49.60 | 33.95 | 24.6 | 1.460972 | | | |
| | | 49.68 | 34.00 | 24.6 | 1.461176 | | | |
| | | 49.49 | 33.87 | 24.6 | 1.461175 | | | |
| | | 49.24 | 33.70 | 24.6 | 1.461127 | | | |
| | | | | | Avc 1.461075 | ±0.000119 | .9532 ±0.0001 | 0.0081 |
| 4 | 46,37938 | 49.58 | 32.52 | 25.0 | 1.524600 | | | |
| | | 49.31 | 32.34 | 25.0 | 1.524737 | | | |
| | | 49.69 | 32.58 | 25.0 | 1.525168 | | | |
| | | 49.25 | 32.30 | 25.0 | 1.524767 | | | |
| | | 49.73 | 32.61 | 25.0 | 1.524092 | | | |
| | | | | | Avc 1.524852 | ±0.000255 | .9575 ±0.0002 | 0.0167 |
| 5 | 50.44918 | 49.67 | 33.05 | 24.6 | 1.502874 | | | |
| | | 49.58 | 32.99 | 24.6 | 1.502879 | | | |
| | | 49.79 | 33.13 | 24.6 | 1.502867 | | | |
| | | 49.73 | 33.09 | 24.7 | 1.502870 | | | |
| | | 49.48 | 32.92 | 24.7 | 1.503037 | | | |
| | | | | | Avc 1.502905 | ±0.00007388 | .9590 ±0.0001 | 0.00491 |
| 6 | 47.88200 | 49.59 | 32.71 | 24.6 | 1.516050 | | | |
| | | 49.83 | 32.86 | 24.6 | 1.516433 | | | |
| | | 49.49 | 32.64 | 24.6 | 1.516237 | | | |
| | | 49.63 | 32.72 | 24.6 | 1.516809 | | | |
| | | 49.67 | 32.75 | 24.6 | 1.516641 | | | |
| | | | | | Avc 1.516434 | ±0.000304 | .9572 ±0.0002 | 0.0200 |
| 7 | 47.53866 | 49.60 | 32.69 | 24.6 | 1.517283 | | | |
| | | 49.64 | 32.72 | 24.5 | 1.517114 | | | |
| | | 49.38 | 32.54 | 24.5 | 1.517516 | | | |
| | | 49.27 | 32.47 | 24.4 | 1.517400 | | | |
| | | 49.83 | 32.83 | 24.5 | 1.517819 | | | |
| | | | | | Avc 1.517426 | ±0.000265 | .9539 ±0.0002 | 0.0174 |
| 8 | 50.35638 | 49.89 | 33.22 | 24.5 | 1.50180 | | | |
| | | 49.53 | 32.97 | 24.5 | 1.50227 | | | |
| | | 49.69 | 33.07 | 24.5 | 1.50257 | | | |
| | | 49.83 | 33.16 | 24.5 | 1.50271 | | | |
| | | 49.24 | 32.78 | 24.4 | 1.50213 | | | |
| | | | | | Avc 1.502296 | ±0.000361 | .9552 ±0.0002 | 0.0240 |
| 9 | 50.82030 | 49.11 | 32.70 | 22.4 | 1.5018348 | | | |
| | | 49.05 | 32.66 | 22.4 | 1.5018371 | | | |
| | | 50.005 | 33.285 | 22.4 | 1.5023283 | | | |
| | | 49.285 | 32.81 | 22.5 | 1.5021334 | | | |
| | | 49.245 | 32.785 | 22.5 | 1.5020588 | | | |
| | | | | | Avc 1.5020384 | ±0.000209 | .9631 ±0.0001 | 0.0139 |
| 10 | 51.12452 | 50.02 | 33.37 | 23.0 | 1.498951 | | | |
| | | 49.265 | 32.87 | 23.0 | 1.498783 | | | |
| | | 49.195 | 32.82 | 23.0 | 1.498934 | | | |
| | | 49.14 | 32.785 | 23.1 | 1.49886 | | | |
| | | 49.15 | 32.79 | 23.1 | 1.49893 | | | |
| | | | | | Avc 1.49889 | ±0.0001324 | .9579 ±0.0001 | 0.00883 |
| 11 | 51.74651 | 49.65 | 33.205 | 23.0 | 1.495257 | | | |
| | | 49.31 | 32.97 | 23.0 | 1.495602 | | | |
| | | 49.325 | 32.98 | 23.0 | 1.495603 | | | |
| | | 49.14 | 32.86 | 23.0 | 1.495435 | 1.495435 | | |
| | | 49.22 | 32.905 | 23.0 | 1.495821 | | | |
| | | | | | Avc 1.495549 | ±0.000211 | .9581 ±0.0001 | 0.0141 |
| 12 | 55.45521 | 49.055 | 33.305 | 23.0 | 1.472902 | | | |
| | | 49.175 | 33.385 | 23.0 | 1.472967 | | | |
| | | 49.39 | 33.535 | 22.9 | 1.472789 | | | |
| | | 49.09 | 33.33 | 22.9 | 1.472847 | | | |
| | | 49.36 | 33.515 | 22.9 | 1.472773 | | | |
| | | | | | Avc 1.472856 | ±0.00008 | .9507 ±0.0001 | 0.0055 |
| 13 | 46.65288 | 49.095 | 32.21 | 22.8 | 1.524216 | | | |
| | | 49.275 | 32.33 | 22.8 | 1.524126 | | | |
| | | 49.30 | 32.34 | 22.8 | 1.524428 | | | |
| | | 49.115 | 32.22 | 22.9 | 1.524364 | | | |
| | | 49.225 | 32.29 | 22.9 | 1.524466 | | | |
| | | | | | Avc 1.524320 | ±0.00014 | .9615 ±0.0001 | 0.00947 |

[1] Original pressure in gas reservoir.
[2] Equalized pressure in gas reservoir and sample call.
[3] $P_1/P_2$
[4] This value refers to the precision of the ratio of the reservoir pressure to the system pressure, expressed as one standard deviation.
[5] The average percentage error in thirteen determinations was 0.0147%.

EXAMPLE II

To establish the reproducibility of values determined by the method of Example I as compared with values obtained by the annealed density method of ASTM D-1505-63T, densities were determined on polymer samples in the form supplied. Densities of the same samples then were determined by ASTM D-1505-63T. Sample 1 was a porous ethylene-hexene-1 copolymer produced in a pilot plant particle form loop reactor. Sample 2 was a standard pellet of high density ethylene polymer supplied by the National Bureau of Standards. Sample 3 was a pellet of low density ethylene homopolymer obtained from a commercial source. Sample 4 was a pellet form of polypropylene obtained from a commercial source. The results are shown in Table II.

Table II

| Sample | ASTM Method | Method of Invention |
|---|---|---|
| 1 | .9620 | .9622 |
| 2 | .9570 | .9561 |
| 3 | .9245 | .9240 |
| 4 | .9080 | .9096 |

These results of Table II are in quite good agreement. The ASTM value of Sample 4 is believed to be too low by reason of poor annealing of the sample.

What is claimed is:

1. Apparatus to measure the density of a particulate porous polymer sample consisting essentially of;
   a. a sample cell of fixed volume including means for admitting and discharging gas therefrom,
   b. a sample container of fixed weight adapted to fit within the sample cell,
   c. a gas reservoir of fixed volume having a valve to admit gas thereto,
   d. a valved line providing gas communication between the sample cell and the gas reservoir,
   e. first instrument means associated with the sample cell to measure the weight of the sample container and generate a signal responsive thereto,
   f. second instrument means associated with the gas reservoir to measure the gas pressure therein and generate a signal responsive thereto, and
   g. computing means, including elements, to;
      (1) receive signals from the first instrument means and calculate the weight of a sample in the sample container,
      (2) receive signals from the second instrument means and calculate gas pressures therefrom,
      (3) calculate the free gas volume in the gas reservoir and the sample cell from the gas pressure of the gas reservoir, when isolated from the sample cell, and the gas pressure of the gas reservoir when in gas communication with the sample cell,
      (4) calculate the volume of a sample in the sample container from the free gas volume determined in g(3) and the known volumes of the gas reservoir and the sample cell,
      (5) calculate the density of the sample from the sample weight determined in g(1) and the sample volume determined in g(4), and
      (6) generate a signal indicating the density of the sample.

2. Apparatus of claim 1 in which the first instrument means is a linear variable differential transducer and the second instrument means is a variable capacitance quartz crystal.

3. Apparartus of claim 1 including a printer which prints the sample density indicated by the signal generated by element g(6).

4. Apparatus of claim 1 including a light emitting diode which displays the sample density indicated by the signal generated by element g(6).

5. Apparatus of claim 1 including pneumatic means for charging porous particulate polymer to the sample container and means for evacuating porous particulate polymer from the sample cell.

6. A method for determining the density of a particulate porous polymer which consists essentially of the steps of:
   a. placing a sample of a particulate porous olefin polymer in a sample container of known weight,
   b. placing the filled sample container in a sample cell of known volume which has a gas inlet and a gas outlet,
   c. placing the sample cell of (b) in open gas communication with a gas reservoir of known volume which has a gas inlet and a gas outlet,
   d. passing helium through the gas reservoir and the sample cell to sweep the gas reservoir and sample cell free of gases other than helium, including any gases absorbed on the polymer sample,
   e. closing the inlet and the outlet of the sample cell,
   f. weighing the sample container and determining the weight of the polymer sample,
   g. pressurizing the gas reservoir to superatmospheric pressure with helium, sealing the inlet to the gas reservoir, and determining the helium pressure within the gas reservoir,
   h. opening the gas reservoir to gas communication with the sample cell and determining the equalized helium pressure in the gas reservoir and the sample cell,
   i. determining the free gas volume in the gas reservoir and the sample cell from the pressures measured in steps (g) and (h),
   j. determining the volume of the polymer sample by subtracting the free gas volume determined in step (i) from the known combined volume of the gas reservoir and the sample cell, and
   k. determining the density of the polymer sample by dividing the weight of the polymer determined in step (f) by the volume of the polymer determined in step (j).

7. The process of claim 6 in which the sample weight is measured by first instrument means which generate a signal indicating the sample weight, the gas pressures are measured by second instrument means which generate signals indicating such pressures, and the signals from said first and second instrument means are fed to computing means which calculate the sample weight, the sample volume, and the density of the polymer sample, and generate a signal indicating the polymer sample's density.

8. A method for determining the density of a particulare porous olefin polymer having hydrocarbon and/or air absorbed in the pores thereof which consists essentially of:
   a. placing a sample of the porous particulate olefin polymer in a sample container of known weight,
   b. placing the sample container of step (a) in a gas tight sample cell of known volume,
   c. pressurizng the sample cell with helium under superatmospheric pressure to displace hydrocarbon and/or air from the pores of the polymer, d. venting helium from the sample cell,
e. repeating steps (c) and (d) until the polymer sample reaches constant weight,
f. determining the weight of the polymer sample after step (e),
g. charging a gas reservoir of known volume with helium under superatmospheric pressure and measuring the pressure thereof,
h. admitting helium from the gas reservoir to the sample cell and measuring the equalized pressure established in the gas reservoir and the sample cell,
i. determining the free gas volume of the gas reservoir and the sample cell containing the polymer sample from the pressures measured in steps (g) and (h),
j. determining the volume of the polymer sample by subtracting the free gas volume determined in step (i) from the known combined volume of the gas reservoir and the sample cell, and
k. determining the density of the polymer from the sample volume determined in step (j) and the sample weight determined in step (f).

9. In a continuous process for preparing a copolymer of ethylene and a mono-1-olefin containing three or more carbon atoms by a particle form process, the improvement of maintaining the polymer density within a narrow preselected range of density which consists essentially of:
 a. withdrawing a slurry of polymer particles from the polymerization reactor,
 b. transferring the sample from (a) to a sample container of known weight, said sample container being placed in a sample cell of known volume,
 c. pressuring the sample cell with helium under superatmospheric pressure,
 d. venting helium from the sample cell,
 e. repeating steps (c) and (d) until the polymer sample reaches constant weight,
 f. determining the weight of the polymer sample after step (e),
 g. charging a gas reservoir of known volume with helium under superatmospheric pressure and measuring the pressure thereof,
 h. admitting helium from the gas reservoir to the sample cell and measuring the equalized pressure in the gas reservoir and the sample cell,
 i. determining the free gas volume of the gas reservoir and the sample cell containing the polymer sample from the pressures measured in steps (g) and (h),
 j. determining the volume of the polymer sample by subtracting the free gas volume determined in step (i) from the known combined volume of the gas reservoir and the sample cell,
 k. determining the true density of the polymer from the sample volume determined in step (j) and the sample weight determined in step (f),
 l. making any required adjustment in the rate of feed of the mono-1-olefin to the reactor to bring the density of the ethylene/mono-1-olefin copolymer within the preselected range, and
 m. repeating steps (a) – (l) on a periodic basis.

10. The process of claim 9 in which a signal indicating the polymer sample's density is generated and fed to control means which make any indicated change in the rate of feed of the mono-1-olefin to the reactor.

* * * * *